United States Patent [19]

Hagstam et al.

[11] Patent Number: 5,047,398

[45] Date of Patent: Sep. 10, 1991

[54] DDAVP ANTIDIURETIC AND METHOD THEREFOR

[75] Inventors: Helmer Hagstam, Malmo, Sweden; Hans Vilhardt, Espergarde, Denmark

[73] Assignee: Ferring B.V., Haarlen, Netherlands

[21] Appl. No.: 809,937

[22] Filed: Dec. 17, 1985

Related U.S. Application Data

[63] Continuation of Ser. No. 705,701, Feb. 26, 1985, abandoned, which is a continuation of Ser. No. 613,779, May 24, 1984.

[30] Foreign Application Priority Data

Nov. 18, 1983 [SE] Sweden .............................. 8306367

[51] Int. Cl.$^5$ .............................................. A61K 37/34
[52] U.S. Cl. ........................................ 514/15; 514/807
[58] Field of Search .................................. 514/807, 15

[56] References Cited

U.S. PATENT DOCUMENTS 3,454,549 7/1969 Boissonnas ........................... 514/807
3,497,491 2/1970 Zaoral ................................... 514/807

OTHER PUBLICATIONS

Kinter et al, cited in Chem. Abstracts, vol. 97:193479x 1982.
American Heritage Dictionary 2nd ed p. 924.
Remingtons Pharm. Sciences 15th Ed. (1975) pp. 83 & 84.

*Primary Examiner*—Jacqueline Stone
*Attorney, Agent, or Firm*—Hopgood, Calimafde, Kalil, Blaustein & Judlowe

[57] ABSTRACT

There is disclosed, in one aspect, an antidiuretic composition in oral dosage form for humans. This composition comprises an antidiuretically effective amount of 1-deamino-8-D-arginine vasopressin (DDAVP) and a pharmaceutically acceptable carrier. The composition is capable of dissolving and being absorbed in the gastrointestinal tract of a human. The composition isused in tablet, capsule, or other generally accepted oral dosage form and generally from about 50 to about 200 micrograms of DDAVP is used per unit dosage In another aspect, there is disclosed a method for treating diabetes insipidus. This method comprises orally administering an antidiuretically effective amount of DDAVP to a human. The DDAVP is substantially dissolved and absorbed in the gastrointestinal tract of the person so treated.

11 Claims, No Drawings

DDAVP ANTIDIURETIC AND METHOD THEREFOR

CROSS REFERENCE TO RELATED APPLICATIONS

This application is a continuation of our application Ser. No. 705,701 filed Feb. 26, 1985 which, in turn, is a continuation of our application Ser. No. 613,779 which was filed on May 24, 1984.

Background of the Invention

This invention relates generally to antidiuretic compositions and methods for treating humans with said compositions. In particular, this invention relates to the antidiuretic compound 1-deamino-8-D-arginine vasopressin, which is commonly known as DDAVP.

DDAVP exhibits a high and specific antidiuretic activity and is useful in treating diabetes insipidus as disclosed in U.S. Pat. No. 3,497,491.

It has been traditionally accepted that proteins and peptides, such as DDAVP, are decomposed in the stomach and intestines without substantial, or any, absorption taking place. Thus, peptide and protein-based pharmaceuticals have been traditionally administered subcutaneously or via absorption through the mucous membranes of the nose or mouth. The above-noted U.S. Pat. No. 3,497,491 discloses that DDAVP is preferably administered subcutaneously or intranasally.

The present most common form for administering DDAVP requires the use of a rhinyle. A rhinyle is a graded plastic tube. The appropriate amount of a solution to be administered is drawn into this tube. Then one end is placed into the nostril and the other end is placed into the mouth. The contents of the tube may thus be aspirated intranasally. This mode of administration is difficult to carry out for some patients, particularly elderly patients. Furthermore, intranasal administration adversely affects the cilia such that virus and bacteria may more readily pass to the mucosa.

Also, DDAVP in its dry form is stable but when used in solution form, the solution should be refrigerated and a preservative added to the solution.

DDAVP solutions may also be administered via a conventional pump spray. Dosage is unreliable with this device, however, and there is a fair amount of waste when the contents in the bottle are reaching an end. The so-called sublingual tablet is also objectionable since it requires a relatively long dissolving time and is dependent upon a patient's saliva secretion.

The search has continued for improved DDAVP compositions useful for oral administration to humans for gastrointestinal absorption and methods of administering these compositions. This invention was made as a result of this search.

OBJECTS AND SUMMARY OF THE INVENTION

Accordingly, it is a general object of the present invention to avoid or substantially alleviate the abovedescribed problems of the prior art.

A more specific object of the invention is to provide DDAVP compositions in a single dosage form for oral administration.

Another object of the invention is to provide DDAVP compositions which dissolve in the gastrointestinal tract in order to allow for the gastrointestinal absorption of DDAVP.

Yet another object of the present invention is to provide DDAVP compositions in a stable form without the need for preservatives and/or refrigeration.

A further object of the invention is to provide a method for orally administering DDAVP.

Another object of the present invention is to provide a method for orally administering DDAVP in a safe and simple manner.

Still other objects and advantages of the present invention will become apparent from the following summary of the invention and description of its preferred embodiment.

The present invention provides, in one aspect, an antidiuretic composition in oral dosage form for humans. This composition comprises an antidiuretically effective amount of DDAVP and a pharmaceutically acceptable carrier. The composition is capable of dissolving and being absorbed in the gastrointestinal tract of a human.

In another aspect, the present invention provides a method for treating diabetes insipidus. This method comprises orally administering an antidiuretically effective amount of DDAVP to a human. The DDAVP dissolves and is absorbed in the gastrointestinal tract of a human.

DESCRIPTION OF THE PREFERRED EMBODIMENT

The antidiuretic effect of the DDAVP used in this invention is most likely due to absorption of the intact DDAVP molecule since any enzymatic destruction of the peptide-binding or of the disulphide bridge in DDAVP leads inevitably to biological inactivation. In the present invention, the peroral doses of DDAVP used to initiate antidiuresis are only slightly higher than the amounts of DDAVP used intranasally by patients who are suffering from diabetes insipidus to control their polyuria.

In the composition of the present invention, an antidiuretically effective amount of DDAVP in oral dosage form may be used. This amount is typically from about 50 to about 200, and preferably from about 50 to about 100 micrograms of DDAVP, based upon an assumed 70 kilogram weight of a mature adult, per each oral dosage unit. This oral dosage unit should be taken two or three times daily.

The composition may be in any form for oral administration including tablets, capsules or other forms known to those skilled in this art. The tablet form is preferred.

Other ingredients well known to those skilled in this art may be used in these compositions. These ingredients include well known fillers and other inert constituents.

The present invention is further illustrated by the following EXAMPLES and COMPARATIVE EXAMPLE.

EXAMPLES 1 and 2

Two tablets are prepared containing the following ingredients:

| Ingredient | Example 1 | Example 2 |
| --- | --- | --- |
| DDAVP (synthesized by Ferring AB) ($\mu$gs.) | 50 | 100 |
| Mannitol USP XX (mgs.) | 39 | 78 |
| Lactose (Ph. Eur. II) (mgs.) | 60 | 60 |
| Microcrystalline cellulose (mgs.) | 60 | 60 |
| Crosslinked carboxymethylcellulose | 2 | 2 |

| Ingredient | Example 1 | Example 2 |
|---|---|---|
| (mgs.) | | |
| Talcum (Ph. Eur. III) (mgs.) | 8 | 8 |
| Magnesium Stearate (Ph. Eur. III) (mgs.) | 2 | 2 |

The microcrystalline cellulose AVICEL PHIOI is a highly purified particulate form of cellulose which is commercially available from FMC Corporation, Philadelphia, Penna. The crosslinked carboxymethylcellulose is Ac-Di-Sol sodium carboxymethylcellulose which is also commercially available from FMC Corporation.

In addition to the above, small amounts of polyvinyl-pyrrolidone-ethanol are used as the binding agent in making the tablets.

The tablets were administered to three patients who suffer from diabetes insipidus. The administration took place for a period of more than 3 months. The dose required to keep the polyuria under control for these patents was 2 to 3 of the 100 microgram tablets every 24 hours. No side-effects were observed. The patients preferred the tablet administration to the conventional intranasal administration of DDAVP.

COMPARATIVE EXAMPLE

The effect of orally administering DDAVP was compared with the effect of orally administering 1-deamino-4-asparagine-8-D-arginine-vasopressin (4-Asn-DDAVP) as follows:

Ten healthy subjects of both sexes, aged 18 through 43 were treated with DDAVP and 4-Asn-DDAVP.

One to two hours after a normal breakfast, the subjects were hydrated by drinking the volume of tap water that corresponded to 2% of their body weight. Every 15 minutes, urine was collected and its volume and osmolality were measured using an Advanced Osmometer Model 3D11. In order to overhydrate themselves, the subjects substituted their loss of fluid by drinking a volume of tap water that corresponded to the amount of urine collected. After about 40 to 45 minutes, the diuresis increased to about 200 milliliters per 15 minute period. At that time, DDAVP or 4-Asn-DDAVP in amounts of from 20 to 200 micrograms was administered perorally in 50 milliliters of distilled water. The DDAVP and 4-Asn-DDAVP were supplied by Ferring AB in lyophilized powder form which could easily be dissolved in water. The water diuresis was followed continually up to 6 hours.

Two of the subjects were supplied with a duodenal tube which was inserted through the nose. The end of the tube was placed with the help of X-rays in the distal part of the duodenum. Overhydration and urine sampling were then carried out as described above.

Urine volumes exceeding 200 milliliters per 15 minutes were taken as an indication that endogen secretion of vasopressin had been maximally suppressed. After this, 200 micrograms of DDAVP dissolved in 10 milliliters of water were injected through a tube.

These investigations illustrate that there is a dosedependent effect of DDAVP, both on the magnitude and duration (the effect lasted at least 6 hours) of the response. A therapeutic effect was obtained with a 20 microgram dosage of DDAVP. Those who were administered DDAVP through the duodenal tube had an immediate antidiuretic response when a corresponding increase in the osmolality and conductivity of the urine was observed. Apart from a slight feeling of tension in the stomach in connection with the initial overhydration, no side-effects were experienced by any of the subjects.

In contrast to the above results with DDAVP, the oral administration of 4-Asn-DDAVP in doses of from 20 to 200 micrograms provides only a moderate, extremely short-lived, effect with only the highest dose. Moreover, a dose of 100 micrograms gave no therapeutic effect.

The principles, preferred embodiments and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. An antidiuretic composition for humans comprising a gastrointestinally absorbable, antidiuretically effective, amount of 1-deamino-8-D-arginine vasopressin and a pharmaceutically acceptable carrier in solid oral dosage form for absorption in the gastrointestinal tract of said humans.

2. The composition of claim 1 wherein said composition is in the form of a tablet.

3. The composition of claim 1 wherein said composition is in the form of a capsule.

4. The composition of claim 1 wherein the amount of said dosage of 1-deamino-8-D-arginine vasopressin is from about 50 to about 200 micrograms per 70 kilogram human per dosage.

5. The composition of claim 4 wherein the amount of said dosage of 1-deamino-8-D-arginine vasopressin is from about 50 to about 100 micrograms per 70 kilogram human per dosage.

6. A method for initiating antidiuresis comprising administering a gastrointestinally adsorbable, antidiuretically effective, amount of 1-deamino-8-D-arginine vasopressin to a human for absorption in the gastrointestinal tract of said human.

7. The method of claim 6 wherein the amount of said 1-deamino-8-D-arginine vasopressin is from about 50 to about 200 micrograms per 70 kilogram human per dosage.

8. The method of claim 7 wherein the amount of said 1-deamino-8-D-arginine vasopressin is from about 50 to about 100 micrograms per 70 kilogram human per dosage.

9. The method of claim 6 wherein said 1-deamino-8-D-arginine vasopressin is administered in the form of a tablet.

10. The method of claim 6 wherein said 1-deamino-8-D-arginine vasopressin is administered in the form of a capsule.

11. A method for treating diabetes insipidus comprising administering a gastrointestinally absorbable, antidiuretically effective, amount of 1-deamino-8-D-arginine vasopressin to a human for absorption in the gastrointestinal tract of said human.

* * * * *

UNITED STATES PATENT AND TRADEMARK OFFICE
CERTIFICATE OF CORRECTION

PATENT NO.   : 5,047,398
DATED        : September 10, 1991
INVENTOR(S)  : Helmer Hagstam et al.

It is certified that error appears in the above-identified patent and that said Letters Patent is hereby corrected as shown below:

Column 4,
Line 43, delete "adsorbable" and insert -- absorbable --.

Signed and Sealed this

Twenty-sixth Day of October, 2004

JON W. DUDAS
*Director of the United States Patent and Trademark Office*